US011793225B2

(12) United States Patent
Ove Von Husby et al.

(10) Patent No.: US 11,793,225 B2
(45) Date of Patent: Oct. 24, 2023

(54) PROCESS FOR PREPARING MIXTURES COMPRISING VANILLIN AND ETHYL VANILLIN

(71) Applicant: Borregaard AS, Sarpsborg (NO)

(72) Inventors: Kurt Ove Von Husby, Sarpsborg (NO); Stian Rosså, Sarpsborg (NO); Peter Ong, Sarpsborg (NO)

(73) Assignee: Borregaard AS, Sarpsborg (NO)

( * ) Notice: Subject to any disclaimer, the term of this patent is extended or adjusted under 35 U.S.C. 154(b) by 756 days.

(21) Appl. No.: 16/306,300

(22) PCT Filed: May 16, 2017

(86) PCT No.: PCT/EP2017/061704
§ 371 (c)(1),
(2) Date: Nov. 30, 2018

(87) PCT Pub. No.: WO2017/207265
PCT Pub. Date: Dec. 7, 2017

(65) Prior Publication Data
US 2019/0166900 A1 Jun. 6, 2019

(30) Foreign Application Priority Data

May 31, 2016 (EP) .................................... 16172098

(51) Int. Cl.
| A23P 10/22 | (2016.01) |
| A23L 27/00 | (2016.01) |
| A23L 27/20 | (2016.01) |
| A23P 10/43 | (2016.01) |
| A61K 8/34 | (2006.01) |
| A61Q 13/00 | (2006.01) |
| A61K 8/02 | (2006.01) |

(52) U.S. Cl.
CPC .............. *A23P 10/22* (2016.08); *A23L 27/20* (2016.08); *A23L 27/204* (2016.08); *A23L 27/70* (2016.08); *A23P 10/43* (2016.08); *A61K 8/347* (2013.01); *A61Q 13/00* (2013.01); *A23V 2002/00* (2013.01); *A23V 2200/208* (2013.01); *A23V 2250/5114* (2013.01); *A23V 2300/31* (2013.01); *A61K 8/0275* (2013.01)

(58) Field of Classification Search
CPC .......... A23P 10/22; A23P 10/43; A23L 27/70; A23L 27/20; A23L 27/204; A61K 8/347; A61K 8/0275; A61Q 13/00; A23V 2002/00; A23V 2200/208; A23V 2250/5114; A23V 2300/31
USPC ......................... 426/534, 538, 650, 555, 453
See application file for complete search history.

(56) References Cited

U.S. PATENT DOCUMENTS

| 6,184,421 B1 | 2/2001 | Metivier | |
| 2012/0277321 A1* | 11/2012 | Le-Thiesse | ............ C11B 9/0061 |
| | | | 514/770 |
| 2013/0203863 A1 | 8/2013 | Le-Thiesse et al. | |
| 2014/0220214 A1 | 8/2014 | Le-Thiesse et al. | |

FOREIGN PATENT DOCUMENTS

| CN | 102596877 A | 7/2012 |
| RU | 2194032 C2 | 12/2002 |
| RU | 2264130 C2 | 11/2005 |
| WO | WO-2015/0028784 A1 | 3/2015 |
| WO | WO-2017/207265 A1 | 12/2017 |

OTHER PUBLICATIONS

NPL2022-000873, Handbook of Food Powders Abstract by B.Cuq 2013.*
International Search Report, PCT/EP2017/061704, (Process for Preparing Mixtures Comprising Vanillin and Ethyl Vanillin, filed May 16, 2017), issued by ISA/European Patent Office, 3 pages, dated Jul. 6, 2017.
Written Opinion, PCT/EP2017/061704, (Process for Preparing Mixtures Comprising Vanillin and Ethyl Vanillin filed May 16, 2017), issued by ISA/European Patent Office, 5 pages, dated Jul. 6, 2017.

* cited by examiner

*Primary Examiner* — Leslie A Wong
(74) *Attorney, Agent, or Firm* — Choate, Hall & Stewart LLP; Michael D. Schmitt

(57) ABSTRACT

The present invention relates to a process for preparing a mixture comprising vanillin and ethyl vanillin which process comprises the steps of (i) mixing at least vanillin powder and ethyl vanillin powder, (ii) keeping the mixture obtained in step (i) in a vessel in order to let the vanillin and ethyl vanillin agglomerate, and (iii) breaking down at least one agglomerate obtained in step (ii) into smaller particles. The present invention also relates to a powdery mixture comprising vanillin and ethyl vanillin obtained by the process according to the present invention.

20 Claims, 2 Drawing Sheets

PROCESS FOR PREPARING MIXTURES COMPRISING VANILLIN AND ETHYL VANILLIN

PRIORITY APPLICATIONS

This application is a national stage entry, under 35 U.S.C. § 371, of PCT/EP2017/061704, filed on May 16, 2017, entitled PROCESS FOR PREPARING MIXTURES COMPRISING VANILLIN AND ETHYL VANILLIN, which claims priority to EP 16172098.2, filed on May 31, 2016, the disclosures of which are hereby incorporated by reference herein in their entireties.

The present invention relates to a process for preparing a mixture comprising vanillin and ethyl vanillin which process comprises the steps of (i) mixing at least vanillin powder and ethyl vanillin powder, (ii) keeping the mixture obtained in step (i) in a vessel in order to let the vanillin and ethyl vanillin agglomerate, and (iii) breaking down at least one agglomerate obtained in step (ii) into smaller particles. The present invention also relates to a powdery mixture comprising vanillin and ethyl vanillin obtained by the process according to the present invention.

BACKGROUND OF THE INVENTION

Vanillin is widely used in a number of industrial fields such as food industry, animal feed industry, pharmacy and perfumery as flavoring agent and/or fragrance.

Vanillin is often combined with ethyl vanillin which is known to intensify the organoleptic properties of vanillin. Thus, there is a growing demand for ready-made pulverulent mixtures of these two compounds. However, the preparation of such mixtures is problematic. Conventional dry mixing of vanillin and ethyl vanillin powder results in a mixture that is very prone to agglomeration, i.e. to forming lumps, a phenomenon generally referred to as "caking". Agglomeration of pulverulent vanillin/ethyl vanillin mixtures further intensifies during prolonged storage. Such caking is associated with difficulties in industrial handling of vanillin/ethyl vanillin blends and results in products that do not satisfy customer expectations.

Thus, there exists a strong demand for pulverulent mixtures of vanillin and ethyl vanillin that exhibit improved flowability and decreased caking, in particular after long-term storage.

Anti-lumping agents such as silicon dioxide and tricalcium phosphate have been added to blends comprising vanillin and ethyl vanillin, but unsuccessfully. Without wishing to be bound by theory, it is believed that moisture is not the reason for caking of blends comprising vanillin and ethyl vanillin, thus rendering known anti-lumping agents used to prevent caking due to moisture inefficient.

US 2011/0230565 describes a process for preparing a compound based on vanillin and ethyl vanillin. The obtained compound exhibits an X-ray diffraction spectrum and a melting point different from that of vanillin and ethyl vanillin and shows decreased agglomeration as compared to pulverulent mixtures obtained by dry-mixing of vanillin and ethyl vanillin. The process comprises melting a mixture of vanillin and ethyl vanillin in a molar ratio of 2 and co-crystallizing vanillin and ethyl vanillin by cooling the mixture to a temperature of 50° C. at which temperature the mixture is maintained for a prolonged period of time, until the molten mixture has solidified. The process requires careful temperature control and is preferably performed under an inert gas, necessitating special equipment.

US 2014/0220214 describes an alternative process for preparing the compound based on vanillin and ethyl vanillin. The process comprises mixing pulverulent vanillin and ethyl vanillin in a preheated mixer at a temperature below the melting temperature of the obtained compound under isothermal conditions. This process requires careful temperature control and a specialized mixing apparatus.

In view of the prior art, it is an object of the present invention to provide a simplified process for the preparation of a mixture comprising vanillin and ethyl vanillin which mixture exhibits decreased agglomeration or caking upon storage as compared to a mixture obtained by conventional dry-mixing of vanillin and ethyl vanillin.

SUMMARY OF THE INVENTION

The above mentioned object and other objects are achieved by the teaching of the present invention. Surprisingly, it has been found that breaking up a cake of vanillin and ethyl vanillin into smaller particles, which cake is formed during storage of a dry-mixture of vanillin and ethyl vanillin powder, results in a composition that has a strongly decreased tendency of caking again (re-caking), as compared to the initial pulverulent mixture of vanillin and ethyl vanillin.

An initial blend of vanillin and ethyl vanillin was stored in a container for 20 days. Intensive caking, i.e. formation of an agglomerated mass, occurred during storage. The cake was broken down into smaller particles. The obtained pulverulent mixture comprising vanillin and ethyl vanillin was stored for another five years. No caking occurred during this long-term storage.

Thus, in a first aspect, the present invention relates to a process for preparing a mixture comprising vanillin and ethyl vanillin which process comprises the steps of (i) mixing at least vanillin powder and ethyl vanillin powder, (ii) keeping the mixture obtained in step (i) in a vessel in order to let the vanillin and ethyl vanillin agglomerate, and (iii) breaking down at least one agglomerate obtained in step (ii) into smaller particles.

The process is simple and readily transposable to the industrial scale. Importantly, it obviates the need for rigorous temperature control.

In a second aspect, the present invention relates to a powdery mixture comprising vanillin and ethyl vanillin obtained by the process according to the present invention.

Preferred embodiments of the present invention are the subject-matter of the dependent claims.

DETAILED DESCRIPTION OF THE INVENTION

In the following, the invention is described with reference to the enclosed figures, wherein:

FIG. 2 shows the cake upon removal of the vessel.

Figure 1:
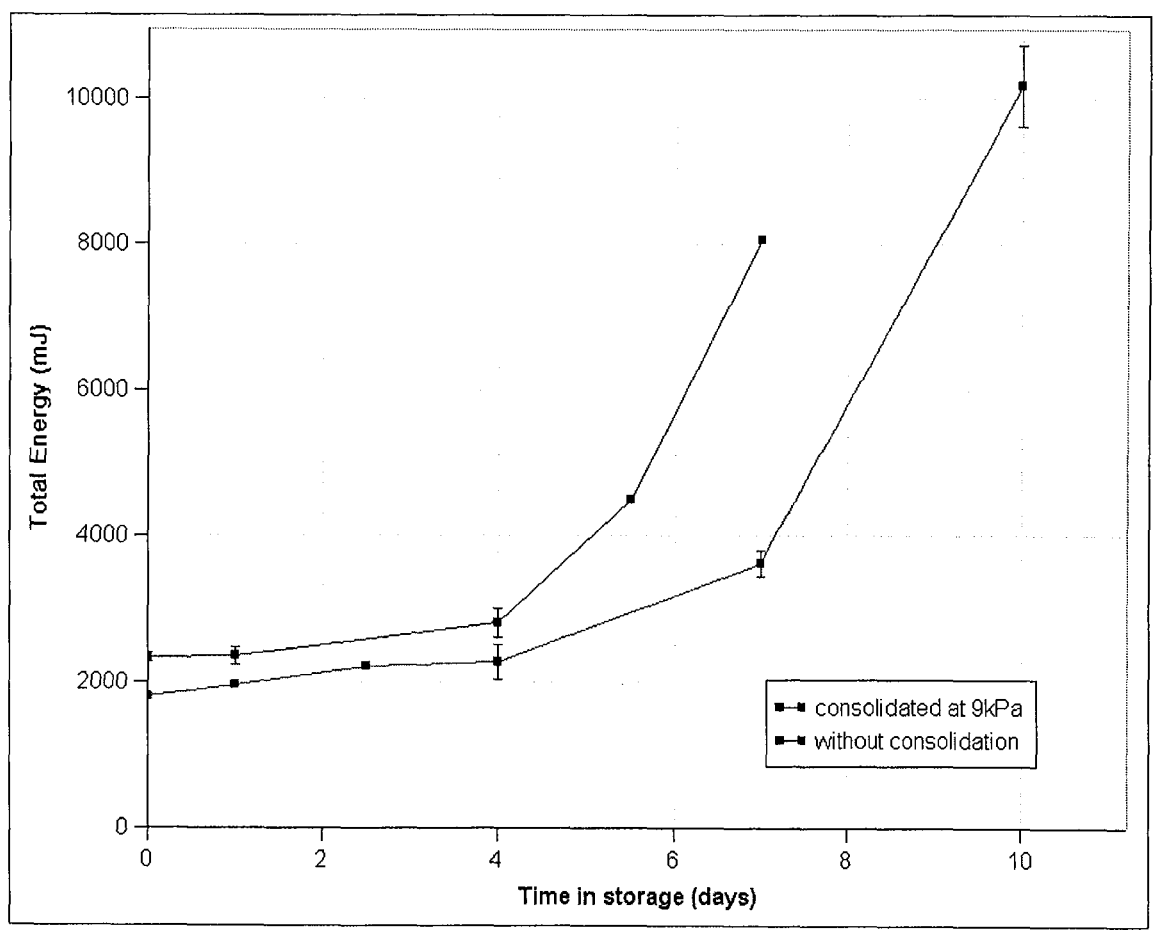
FIG. 1 shows the time dependency of the caking propensity of a 1:1:1 mixture of vanillin, ethyl vanillin and maltodextrin, stored with (upper curve) and without (lower curve) applying a vertical load of 9 kPa to the mixture. The tendency for caking was measured as the resistance of the mixture to flow.

Advantages, preferred embodiments and applications of the present invention are described in the following.

In a first aspect, the present invention relates to a process for preparing a mixture comprising vanillin and ethyl vanillin which process comprises the steps of (i) mixing at least vanillin powder and ethyl vanillin powder, (ii) keeping the mixture obtained in step (i) in a vessel in order to let the vanillin and ethyl vanillin agglomerate, and (iii) breaking down at least one agglomerate obtained in step (ii) into smaller particles.

The term "vanillin" in the context of the present invention refers to 4-hydroxy-3-methoxybenzaldehyde. The term "ethyl vanillin" in the context of the present invention refers to 4-hydroxy-3-ethoxybenzaldehyde. Both vanillin and ethyl vanillin used in the process according to the present invention may be of any source or may have been produced in any way. E.g., vanillin and/or ethyl vanillin may have been produced via any chemical synthesis, irrespective of the starting substrate. Vanillin may also have been produced via a biochemical process. For instance, vanillin may have been produced via a microbiological fermentation process, especially of ferulic acid.

The vanillin and ethyl vanillin starting material to be used in the process according to the present invention is pulverulent, i.e. vanillin and ethyl vanillin are added and mixed with each other in solid powder form. Both vanillin and ethyl vanillin are added at a temperature which is below their respective melting temperature, i.e. below 81° C. for vanillin and 76° C. for ethyl vanillin. The terms "pulverulent" and "powder" in the context of the present invention are used interchangeably and both refer to a substance consisting of particles with a diameter of up to 2 mm.

The term "mixing" in the context of the present invention means combining, in a vessel, at least two different solid pulverulent substances and to blend these substances by any means such that the homogeneity of the distribution of the at least two different substances in the mixture is increased at least to some extent during the process of mixing. Particularly, an essentially homogeneous mixture of the at least two substances is obtained.

Particularly, vanillin and ethyl vanillin are mixed in a mixer, particularly a ploughshare mixer, a paddle mixer, a plow mixer, a ribbon mixer or a band mixer.

The vanillin and the ethyl vanillin powder may be introduced into the mixer simultaneously or one after the other, in any order. The vanillin and ethyl vanillin powder may also be added fractionally, during the entire duration of or during a part of the duration of step (i).

The mixing is performed in the solid phase, i.e. at a temperature below the melting point of ethyl vanillin, i.e. at a temperature below 76° C.

Mixing is preferably performed by stirring, particularly at a stirring speed of 5 to 200 rpm, more particularly 35 to 50 rpm.

Step (i) preferably yields a substantially homogenous mixture of vanillin and ethyl vanillin, or of vanillin, ethyl vanillin and any other further additive that is added before or during step (i).

Preferably, the mixing is performed at ambient temperature and ambient humidity. The term ambient temperature in the context of the present invention refers to a temperature of from 15 to 32° C., particularly a temperature of from 18 to 30° C., more particularly a temperature of from 20 to 28° C. The term ambient humidity in the context of the present invention refers to a relative humidity of from 25% to 80%, particularly of from 35% to 65%.

In particular embodiments, the mixture obtained in step (i) is kept in said vessel essentially without stirring or mixing in step (ii).

In particular embodiments, the process according to the invention further comprises the step of adding maltodextrin. Maltodextrin addition improves dispersability and flowability of the powder blend. Other types of bulking agents used in known vanillin blends may have poorer flowability properties and can worsen moisture-based caking. The addition of maltodextrin was not observed to affect the caking described in this application substantially In particular embodiments, said maltodextrin is in the form of a powder and is mixed with said vanillin powder and said ethyl vanillin powder in step (i).

In particular other embodiments, said maltodextrin is added after step (iii).

Said maltodextrin may also be added fractionally, i.e. a part of said maltodextrin may be added before and/or during step (i) and another part of said maltodextrin may be added after step (iii).

The vanillin and the ethyl vanillin powder and optionally the maltodextrin powder may be mixed in any weight ratio that is suitable for the desired final product, i.e. the weight ratio may be chosen according to the intended use of the final product.

In particular embodiments, the weight ratio of vanillin and ethyl vanillin in the mixture obtained in step (i) is from 99:1 to 1:99, particularly from 98:2 to 2:98, more particularly from 96:4 to 4:96, more particularly from 90:10 to 10:90, more particularly from 70:30 to 30:70.

In particular embodiments, the weight ratio of vanillin: ethyl vanillin:maltodextrin in the mixture obtained in step (i) is 1:0.1-10:0.1-10, particularly 1:0.25-4:0.25-4, more particularly from 1:0.5-2:0.5-2, most particularly about 1:1:1.

The agglomeration in step (ii) was observed to be fastest at a vanillin:ethyl vanillin ratio close to 1:1. The maltodextrin was observed to have minor or only diluting effects on the caking process.

In particular embodiments, the mixture obtained in step (i) consists essentially of vanillin, ethyl vanillin and optionally maltodextrin. In particular embodiments, the mixture obtained in step (i) consists of vanillin, ethyl vanillin and optionally maltodextrin.

In particular embodiments, the process according to the invention further comprises the step of adding at least one further additive, particularly selected from sugars and sugar alcohols, starches, preservatives, hydrocolloids, and aromas (flavor ingredients).

Suitable sugars and sugar alcohols include glucose, sucrose, fructose, galactose, ribose, maltose, lactose, sorbitol, mannitol, xylitol, lactitol, maltitol, oligosaccharides and invert sugars.

Suitable preservatives include antioxidants, particularly vitamin E.

Said at least one further additive may be added in any weight ratio relative to the vanillin and the ethyl vanillin that is suitable for the desired final product, i.e. the weight ratio may be chosen according to the intended use of the final product.

In particular embodiments, said at least one further additive is added before or during step (i). In particular other embodiments, said at least one further additive is added after step (iii).

Said at least one further additive may also be added fractionally, i.e. a part of said additive may be added before and/or during step (i) and another part of said at least one further additive may be added after step (iii).

In particular embodiments, step (i) is performed at a temperature of from 0° C. to 50° C., particularly of from 15°

C. to 35° C., more particularly of from 20° C. to 28° C., most particularly at a temperature of about 20° C.

In particular embodiments, the entire weight of the mixture obtained in step (i) is from 10 kg to 600 kg, particularly from 20 kg to 300 kg.

In particular embodiments, the volume of said vessel in which the mixture obtained in step (i) is kept is from 10 l to 1000 l.

Step (ii) is performed until caking to at least some degree has occurred. Particularly, step (ii) is performed until at least one agglomerate comprising vanillin and ethyl vanillin is formed, which agglomerate has a volume that is at least $10^2$ times, more particularly at least $10^4$ times, more particularly at least $10^6$ times greater than the average volume of the vanillin and ethyl vanillin particles of the mixture obtained in step (i).

In particular embodiments, step (ii) is performed at a temperature of from 0° C. to 50° C., particularly of from 15° C. to 35° C., more particularly of from 20° C. to 28° C., most particularly at a temperature of about 20° C. It is believed that increasing temperatures (but below the melting point of vanillin and ethyl vanillin) speed up the caking process.

In particular embodiments, in step (ii) a vertical load of from 0 to 50 kPa, particularly of from 3 to 30 kPa, more particularly of from 5 to 20 kPa, most particularly of from 8 to 15 kPa is applied to the mixture obtained in step (i).

Said vertical load may be applied by any suitable means including springs, hydraulic balances or weights.

In particular embodiments, in step (ii) the mixture obtained in step (i) is kept in said vessel without stirring or mixing for at least 4, 5, 6, 7, 8, 9, 10, 11, 12, 13, 14, 15, 16, 17, 18, 19, or for at least 20 days.

As can be seen from Example 1 below, the critical time period for caking decreases with an increasing vertical load applied to the mixture obtained in step (i). Any one of ordinary skill in the art is readily able to determine the critical time period for caking of a given mixture comprising vanillin and ethyl vanillin at a given vertical load applied to said mixture.

In particular embodiments, the at least one agglomerate formed in step (ii) comprises at least 20%, particularly at least 30%, more particularly at least 50%, even more particularly at least 75%, most particularly at least 90% of the vanillin and of the ethyl vanillin of the mixture obtained in step (i).

In particular embodiments, the process according to the invention comprises an additional step of separating the at least one agglomerate obtained in step (ii) from vanillin and ethyl vanillin powder not agglomerated, particularly wherein said separation is done by sieving.

The caking process of step (ii) does not have to be complete, i.e. the agglomerate or the agglomerates formed in step (ii) need not encompass the entire vanillin and ethyl vanillin of the mixture obtained in step (i). Preferably, however, step (iii) is performed with a starting material of which the majority is agglomerated, particularly of which at least 50%, more particularly at least 75%, more particularly at least 90%, and most particularly at least 95% are agglomerated, in order to obtain a pulverulent final product containing a high percentage of particles with the desired "anti-caking properties". To this end, the agglomerate or the agglomerates formed in step (ii) may be separated from vanillin and ethyl vanillin powder not agglomerated and may subsequently be used as starting material for step (iii).

The term "agglomerated" in the context of the present invention means being present in a solid agglomerate, which agglomerate has a volume that is at least $10^2$ times, more particularly at least $10^4$ times, more particularly at least $10^6$ times greater than the average volume of the vanillin and ethyl vanillin particles of the mixture obtained in step (i).

In the context of the present invention, the term "smaller particles" means particles of a lower volume than said agglomerate or said agglomerates.

In particular embodiments, said breaking down of the at least one agglomerate in step (iii) is by grinding, crushing, sieving, ultra-sonication, oscillation, slicing, cutting or milling.

Said crushing may be performed in any standard apparatus, such as a toothed roll crusher or a granulator.

Said milling may be performed in any standard apparatus, such as a paddle mill, a pin mill, a blade mill or a hammer mill.

The final product of the process according to the invention is pulverulent, i.e. a solid powder. It shows improved flowability and decreased caking upon storage as compared to an equivalent blend of vanillin and ethyl vanillin obtained by conventional dry-mixing.

In particular embodiments, the average particle diameter of the particles obtained in step (iii) is from 0 to 2 mm, particularly from 10 μm to 1 mm.

In the context of the present invention, the term "particle diameter" of a given particle refers to the diameter of an imaginary sphere that has the same volume as the given particle.

In a second aspect, the present invention relates to a powdery mixture comprising vanillin and ethyl vanillin obtained by the process according to any one of the preceding claims.

It was surprisingly found that the mixture obtained by the process according to the present invention shows increased flowability and decreased caking as compared to equivalent conventional dry-mixtures of vanillin and ethyl vanillin.

In particular embodiments, the powdery mixture obtained by the process according to the invention further comprises maltodextrin.

In a third aspect, the present invention relates to the use of the powdery mixture obtained by the process according to the invention for the manufacture of foodstuff, animal feed, a pharmaceutical composition, a cosmetic composition, a perfume, fragrance or a detergent.

In a further aspect, the present invention relates to the use of the powdery mixture obtained by the process according to the invention as flavorant and/or fragrance, particularly wherein said flavorant and/or fragrance is used in foodstuff or animal feed, in a pharmaceutical composition, in a cosmetic composition, in a perfume or in a detergent.

EXAMPLES

1. Time Dependency of the Caking Propensity of Vanillin/Ethyl Vanillin Blends

In order to evaluate the time dependency of the caking propensity of an 1:1:1 mixture of vanillin, ethyl vanillin and maltodextrin, a series of conditioned 160 ml samples were prepared and stored at ambient temperature and humidity for various time periods. After storage, the total flow energy of the samples was measured by dynamic testing and was plotted against the time in storage as shown in FIG. 1.

The dynamic flow properties were determined by rotating a precision blade down a helical path through the mixture. During this downward traverse the torque and axial force acting on the blade was measured and the resistance to flow was calculated and expressed as total flow energy.

Figure 2:
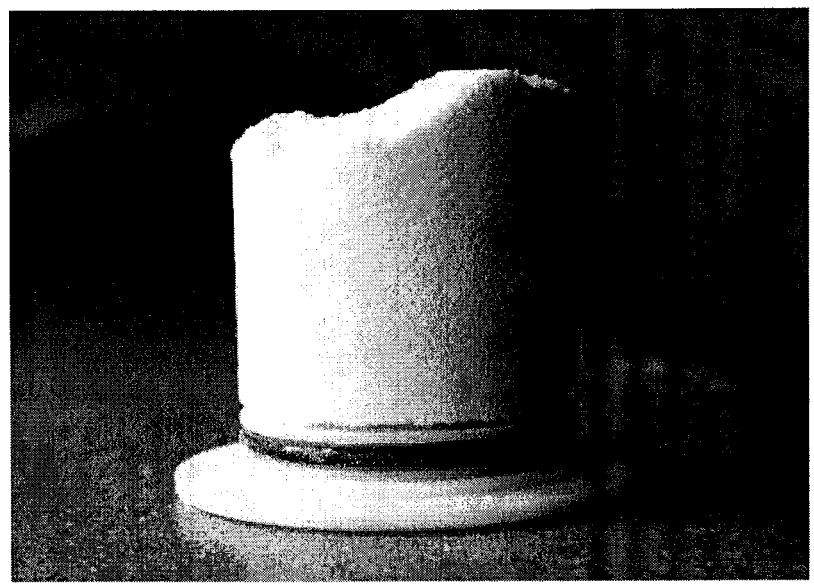
FIG. 2 shows a cake obtained after storing a 1:1:1 mixture of vanillin, ethyl vanillin and maltodextrin in a vessel for 14 days without stirring.

As can be seen in FIG. 1 the flow energy increased with the time in storage and the caking effects significantly accelerated after 7 days. Formation of a very solid cake after 14 days in storage was observed (FIG. 2).

In order to investigate the influence of increased normal load on the powder caking behavior, as would for instance be found in a storage bin, another batch of conditioned samples were consolidated under a normal load of 9 kPa, stored for the same time periods and tested using the same dynamic method as the unconsolidated samples. As can be seen from FIG. 1, powder caking is accelerated under increased normal load. Without wishing to be bound by theory, it is believed that accelerated caking is due to the increased stress acting on the particles/the particle contact points which likely enhances any surface chemical interactions and may increase the number of contact points owing to a greater packing density.

The critical time for cake formation was reduced from about 7 days under low stress conditions (i.e. no vertical load was applied) to about 4 days under higher stress conditions (i.e. a vertical load of 9 kPa was applied).

2. Process for Preparing a Vanillin/Ethyl Vanillin Blend that does not Cake

This example illustrates how the described process efficiently produces a mixture comprising vanillin and ethyl vanillin, which mixture does not cake, even during long-term storage.
1. Vanillin (5 kg) was blended with maltodextrin (52 kg) for 10 minutes in a ribbon blender.
2. Ethyl vanillin (35 kg) and flavor ingredients (8 kg) were added and the mixture was blended for an additional 25 minutes in a ribbon blender.
3. The mixture was stored in 25 kg carton boxes for a period of 480 hours.
4. During this storage, caking of the mixture occurred, i.e. an agglomerated mass was formed.
5. The agglomerated mass was subjected to mechanical oscillation, using a mechanical sieve, to break it down into smaller particles.
6. The mixture was stored in a container for a period of five years. No caking occurred, i.e. no agglomerated mass was formed during this time period.

3. Process for Preparing a Vanillin/Ethyl Vanillin Blend that does not Cake

This example illustrates how the described process efficiently produces different mixtures comprising vanillin and ethyl vanillin, which mixtures do not cake, even during long-term storage.
1. Several mixtures of vanillin and ethyl vanillin are produced. All mixtures have a total weight of 100 kg, but have different proportions, see Table 1.
3. The mixtures are stored in a container for a period of 480 hours.
4. During this storage, caking occurs, i.e. an agglomerated mass is formed in each mixture.
5. The agglomerated mass in each mixture is subjected to mechanical oscillation, to break it down into smaller particles.
6. The mixtures are stored in containers for a period of five years. No caking occurs, i.e. no agglomerated mass is formed during this time period.

TABLE 1

| Sample # | 1 | 2 | 3 | 4 | 5 | 6 | 7 |
| --- | --- | --- | --- | --- | --- | --- | --- |
| Vanillin (kg) | 96 | 90 | 70 | 50 | 30 | 10 | 4 |
| Ethyl vanillin (kg) | 4 | 10 | 30 | 50 | 70 | 90 | 96 |
| Appearance after 5 years | No lumps | No lumps | No lumps | No lumps | No lumps | No lumps | No lumps |

4. Process for Preparing a Vanillin/Ethyl Vanillin Blend that does not Cake

Ethyl vanillin and vanillin were mixed manually (by shaking) in the ratios given in Table 2. The samples were individually transferred to amber 2000 ml jars and kept at ambient conditions for 13 weeks. After that period the glasses were opened and lumps were crushed using a sifter. The samples were again transferred to the same jars and kept for another 15 weeks before the appearance was checked again. The sample overview and results are given in Table 2.

TABLE 2

| Sample # | 1 | 2 | 3 | 4 | 5 | 6 |
| --- | --- | --- | --- | --- | --- | --- |
| Vanillin (g) | 990 | 980 | 960 | 900 | 700 | 500 |
| Ethyl vanillin (g) | 10 | 20 | 40 | 100 | 300 | 500 |
| Appearance after 13 weeks | Lightly packed; no lumps | Lightly packed; a few loose lumps | Somewhat packed | Very packed; more than 7 but less than 5 and 6 | Very packed; need to chisel the product out | Very packed; need to chisel the product out |
| Degree of packing (1-9) | 2 | 4 | 6 | 8 | 9 | 9 |
| Appearance 15 weeks after sifting | No lumps | No lumps | No lumps | No lumps | No lumps | No lumps |

TABLE 2-continued

| Sample # | 7 | 8 | 9 | 10 | 11 |
|---|---|---|---|---|---|
| Vanillin (g) | 300 | 100 | 40 | 20 | 10 |
| Ethyl vanillin (g) | 700 | 900 | 960 | 980 | 990 |
| Appearance after 13 weeks | Packed; less than 5/6; need to chisel the product out | Somewhat packed; can be removed from glass with spatula | Lightly packed; no lumps | Not packed; no lumps | Not packed; no lumps |
| Degree of packing (1-9) | 7 | 5 | 3 | 1 | 1 |
| Appearance 15 weeks after sifting | No lumps | No lumps | No lumps | No lumps | No lumps |

The invention claimed is:

1. A process for preparing a mixture comprising vanillin and ethyl vanillin comprising the steps of:
   (i) mixing at least vanillin powder and ethyl vanillin powder;
   (ii) keeping the mixture obtained in step (i) in a vessel in order to let the vanillin and ethyl vanillin agglomerate; and
   (iii) breaking down at least one agglomerate obtained in step (ii) into smaller particles, wherein in step (ii) the mixture obtained in step (i) is kept in said vessel without stirring or mixing, and the at least one agglomerate obtained in step (ii) is formed during storage of a dry-mixture comprising the vanillin powder and the ethyl vanillin powder.

2. The process according to claim 1, further comprising the step of adding maltodextrin.

3. The process according to claim 2, wherein (a) said maltodextrin is in the form of a powder and is mixed with said vanillin powder and said ethyl vanillin powder in step (i), and/or wherein (b) said maltodextrin is added after step (iii).

4. The process according to claim 1, wherein the weight ratio of vanillin and ethyl vanillin in the mixture obtained in step (i) is from 99:1 to 1:99.

5. The process according to claim 2, wherein the weight ratio of vanillin:ethyl vanillin:maltodextrin in the mixture obtained in step (i) is 1:0.1 to 10:0.1 to 10.

6. The process according to claim 1, wherein the mixture obtained in step (i) consists essentially of vanillin, ethyl vanillin and maltodextrin.

7. The process according to claim 1, further comprising the step of adding at least one further additive selected from the group consisting of sugars and sugar alcohols, starches, preservatives, hydrocolloids, or aromas.

8. The process according to claim 1, wherein step (i) is performed at a temperature of from 0° C. to 50° C.

9. The process according to claim 1, wherein in step (ii) a vertical load of from 0 to 50 kPa is applied to the mixture obtained in step (i).

10. The process according to claim 1, wherein in step (ii) the mixture obtained in step (i) is kept in said vessel without stirring or mixing for at least 4 days and/or wherein the at least one agglomerate formed in step (ii) comprises at least 20% of the vanillin and of the ethyl vanillin of the mixture obtained in step (i).

11. The process according to claim 1, comprising an additional step of separating the at least one agglomerate obtained in step (ii) from vanillin and ethyl vanillin powder not agglomerated.

12. The process according to claim 1, wherein said breaking down the at least one agglomerate in step (iii) is done by grinding, crushing, sieving, ultra-sonication, oscillation, slicing, cutting or milling, or any combination of these.

13. The process according to claim 1, wherein the average particle diameter of the particles obtained in step (iii) is from 0 to 2 mm.

14. The process according to claim 11, wherein said separation is done by sieving.

15. The process according to claim 1, wherein the weight ratio of vanillin and ethyl vanillin in the mixture obtained in step (i) is from 98:2 to 2:98.

16. The process according to claim 1, wherein the weight ratio of vanillin and ethyl vanillin in the mixture obtained in step (i) is from 90:10 to 10:90.

17. The process according to claim 1, wherein the weight ratio of vanillin and ethyl vanillin in the mixture obtained in step (i) is from 70:30 to 30:70.

18. The process according to claim 1, wherein the weight ratio of vanillin : ethyl vanillin : maltodextrin in the mixture obtained in step (i) is 1:0.5 to 2:0.5 to 2.

19. The process according to claim 1, wherein step (i) is performed at a temperature of from 20° C. to 28° C.

20. The process according to claim 1, wherein in step (ii) the mixture obtained in step (i) is kept in said vessel without stirring or mixing for at least at least 20 days.

* * * * *